United States Patent
Choi et al.

(10) Patent No.: US 11,568,539 B1
(45) Date of Patent: Jan. 31, 2023

(54) APPARATUS AND METHOD FOR PROSTATE CANCER ANALYSIS

(71) Applicants: SEOUL NATIONAL UNIVERSITY HOSPITAL, Seoul (KR); Korea University Research and Business Foundation, Seoul (KR); Seoul National University R&DB Foundation, Seoul (KR); PLANIT Healthcare Inc., Seoul (KR)

(72) Inventors: Jinwook Choi, Seoul (KR); Kyoungbun Lee, Seoul (KR); Gyeong Hoon Kang, Seoul (KR); Kyung Chul Moon, Seoul (KR); Gheeyoung Choe, Seongnam-si (KR); Kyu Sang Lee, Seongnam-si (KR); Jeong Hwan Park, Seoul (KR); Won-Ki Jeong, Seoul (KR); Se Young Chun, Seoul (KR); Youngkwan Kim, Seoul (KR)

(73) Assignees: SEOUL NATIONAL UNIVERSITY HOSPITAL, Seoul (KR); KOREA UNIVERSITY RESEARCH AND BUSINESS FOUNDATION, Seoul (KR); SEOUL NATIONAL UNIVERSITY R&DB FOUNDATION, Seoul (KR); PLANIT HEALTHCARE INC., Seoul (KR)

( * ) Notice: Subject to any disclaimer, the term of this patent is extended or adjusted under 35 U.S.C. 154(b) by 0 days.

(21) Appl. No.: 17/857,328

(22) Filed: Jul. 5, 2022

(30) Foreign Application Priority Data

Dec. 30, 2021 (KR) .................. 10-2021-0192094

(51) Int. Cl.
*G06T 7/00* (2017.01)
*G16H 30/40* (2018.01)
(Continued)

(52) U.S. Cl.
CPC ........... *G06T 7/0012* (2013.01); *G16H 30/40* (2018.01); *G16H 50/20* (2018.01); *G16H 70/60* (2018.01);
(Continued)

(58) Field of Classification Search
CPC ......... G06T 7/0012; G06T 2207/20081; G06T 2207/20084; G06T 2207/30081;
(Continued)

(56) References Cited

U.S. PATENT DOCUMENTS

2014/0233826 A1   8/2014  Agaian et al.
2017/0169276 A1*  6/2017  Agaian ................ A61B 5/4381
(Continued)

FOREIGN PATENT DOCUMENTS

KR   10-2020-0016666   2/2020
KR     10-2215269     2/2021
(Continued)

OTHER PUBLICATIONS

M May et al., "Visual estimation of the tumor volume in prostate cancer: a useful means for predicting biochemical-free survival after radical prostatectomy?", Prostate Cancer and Prostatic Diseases (2007) 10, 66-71, Dec. 26, 2006.

(Continued)

*Primary Examiner* — Nay A Maung
*Assistant Examiner* — Jose M Torres
(74) *Attorney, Agent, or Firm* — Lex IP Meister, PLLC

(57) ABSTRACT

Provided is a method of operating an apparatus for prostate cancer analysis operated by at least one processor, the method including: receiving digital slide images prepared from serial sections of a prostatectomy specimen, and a gross image of the serial sections; acquiring prostate cancer-related histological information of each received digital slide image using an artificial neural network model trained to (Continued)

infer histological information from the digital slide images; generating digital pathology images by displaying the prostate cancer-related histological information inferred from the artificial neural network model on each digital slide image; and providing a histological mapping image in which a tumor region extracted from each digital pathology image is mapped to a gross image of the corresponding section.

13 Claims, 12 Drawing Sheets

(51) Int. Cl.
  *G16H 70/60*  (2018.01)
  *G16H 50/20*  (2018.01)
(52) U.S. Cl.
  CPC .............. *G06T 2207/20081* (2013.01); *G06T 2207/20084* (2013.01); *G06T 2207/30081* (2013.01); *G06T 2207/30096* (2013.01)
(58) Field of Classification Search
  CPC .......... G06T 2207/30096; G16H 30/40; G16H 50/20; G16H 70/60
  See application file for complete search history.

(56) References Cited

U.S. PATENT DOCUMENTS

| | | | |
|---|---|---|---|
| 2020/0293748 A1 | 9/2020 | Avenel et al. | |
| 2021/0027459 A1 | 1/2021 | Madabhushi et al. | |
| 2021/0093249 A1* | 4/2021 | Anand | G16H 30/40 |
| 2022/0148169 A1* | 5/2022 | Mermel | A61B 5/7264 |

FOREIGN PATENT DOCUMENTS

| | | |
|---|---|---|
| KR | 10-2021-0038987 | 4/2021 |
| KR | 10-2246319 | 5/2021 |

OTHER PUBLICATIONS

Salarian, Mehmoush, "Prostate Tumor Volume Measurement on Digital Histopathology and Magnetic Resonance Imaging" (2014). Electronic Thesis and Dissertation Repository. 2450.
Wenchao Han et al., "Automatic cancer detection on digital histopathology images of mid-gland radical prostatectomy specimens", Journal of Medical Imaging, Jul. 16, 2020., vol. 7, No. 4, pp. 1-23.
Lucas C. Cahill et al., "Comparing histologic evaluation of prostate tissue using nonlinear microscopy and paraffin H&E: a pilot study", Modern Pathology, Mar. 26, 2019., vol. 32, pp. 1158-1167.
Mirabela Rusu et al., "Registration of pre-surgical MRI and whole-mount histopathology images in prostate cancer patients with radical prostatectomy via RAPSODI", arXiv, Sep. 21, 2019., pp. 1-16.
Ilaria Jansen et al., "Histopathology: ditch the slides, because digital and 3D are on show", World Journal of Urology, Feb. 2, 2018., vol. 36, pp. 549-555.
Gladell P. Paner, MD et al., "Protocol for the Examination of Radical Prostatectomy Specimens From Patients With Carcinoma of the Prostate Gland", College of American Pathologists, Nov. 2021.
Xu-Ying Liu et al., "Exploratory Undersampling for Class-Imbalance Learning", IEEE Transactions on Systems, Man, and Cybernetics—Part B: Cybernetics, vol. 39, No. 2, Apr. 2009.
Wei-Chao Lin et al., "Clustering-based undersampling in class-imbalanced data", Information Sciences 409-410 (2017) 17-26, May 8, 2017.
James A. Diao et al., "Human-interpretable image features derived from densely mapped cancer pathology slides predict diverse molecular phenotypes", Nature Communications 12, 1613 (2021). https://doi.org/10.1038/s41467-021-21896-9.
Olaf Ronneberger et al., "U-Net: Convolutional Networks for Biomedical Image Segmentation", MICCAI 2015, Part II, LNCS 9351, pp. 234-241_Chapter_U-NetConvolutionalNetworksForB.
Mark Sandler et al., "MobileNetV2: Inverted Residuals and Linear Bottlenecks", 2018 IEEE/CVF Conference on Computer Vision and Pattern Recognition, 2018, pp. 4510-4520, doi: 10.1109/CVPR.2018.00474.
Mingxing Tan et al., "EfficientNet: Rethinking Model Scaling for Convolutional Neural Networks", arXiv:1905.11946v5 [cs.LG] Sep. 11, 2020.
Jie Hu et al., "Squeeze-and-Excitation Networks", 2018 IEEE/CVF Conference on Computer Vision and Pattern Recognition, 2018, pp. 7132-7141, doi: 10.1109/CVPR.2018.00745.
Yuchun Li et al., "Automated Gleason Grading and Gleason Pattern Region Segmentation Based on Deep Learning for Pathological Images of Prostate Cancer", IEEE Access, vol. 8, pp. 117714-117725, 2020, doi: 10.1109/ACCESS.2020.3005180.
Wenyuan Li et al., "Path R-CNN for Prostate Cancer Diagnosis and Gleason Grading of Histological Images", IEEE Transactions on Medical Imaging, vol. 38, No. 4, Apr. 2019.

\* cited by examiner

APPARATUS AND METHOD FOR PROSTATE CANCER ANALYSIS

CROSS-REFERENCE TO RELATED APPLICATION

This application claims priority to and the benefit of Korean Patent Application No. 10-2021-0192094 filed in the Korean Intellectual Property Office on Dec. 30, 2021, the whole contents of which are incorporated herein by reference.

BACKGROUND

(a) Field

The present disclosure relates to prostate cancer analysis.

(b) Description of the Related Art

Prostate cancer is reported to be the most common cancer in men in OECD countries such as the United States and the United Kingdom. Although the incidence of prostate cancer in Korea is much lower than that of the United States, it is expected that the increase in prostate cancer will continue due to westernization of lifestyles along with an increase in the elderly population.

The prostate cancer can be diagnosed through histological examination. Histopathological diagnosis is made for tissues obtained by puncturing prostate or by surgical resection. Through histological diagnosis it is possible to predict patient's prognosis. Mandatory reporting items for the histological evaluation of the resected specimens are tumor locations (top, bottom, left, and right), tumor burden, which is the proportion of cancer in prostate tissue. The relationship between the tumor burden and the prognosis is somewhat controversial, but the tumor burden and the prognosis are used for treatment decisions as independent prognostic factors or designated as mandatory reporting items in the CAP Cancer Reporting Protocols of radical prostatectomy specimens recommended by the College of American Pathologists.

The tumor burden is calculated through the pathologist's visual inspection of slide with microscope to determine the proportion occupied by tumor in the whole prostate tissue. Therefore, the tumor burden may have different results depending on the subjectivity of specialist, the tissue sample processing method for each institution, and the glass slide manufacturing method. A difference in the relationship between the tumor burden and the prognosis occurs due to a difference in environment for measuring the tumor burden.

SUMMARY

The present disclosure has been made in an effort to provide an apparatus and a method for prostate cancer analysis based on an artificial intelligence model determining whether or not prostate cancer is present based on sections of a resected prostate tissue, and an operating method thereof.

The present disclosure has been made in an effort to provide a method and apparatus for visually displaying analysis information including a prostate tumor location and tumor burden.

The present disclosure has been made in an effort to provide a method and apparatus for visually displaying a tumor region by histological mapping on a gross image of serial sections.

An exemplary embodiment of the present disclosure provides a method of operating an apparatus for prostate cancer analysis operated by at least one processor, includes receiving digital slide images prepared from serial sections of a prostatectomy specimen, and a gross image of the serial sections; acquiring prostate cancer-related histological information of each received digital slide image using an artificial neural network model trained to infer histological information from the digital slide images; generating digital pathology images to display the prostate cancer-related histological information inferred from the artificial neural network model on each digital slide image; and providing a histological mapping image in which a tumor region extracted from each digital pathology image is mapped to a gross image of the corresponding section.

The providing the histological mapping image may include extracting a tumor region from each digital pathology image, and generating histological mapping information for mapping the extracted tumor region to the gross image of the corresponding section; and providing the histological mapping image by applying the histological mapping information to the corresponding gross image.

The method may further include calculating a tissue area and a tumor area from each digital pathology image, and calculating a tumor burden, which is a ratio of a total tumor area to a total tissue area of the whole digital pathology image.

The calculating of the tumor burden may include calculating the tumor area and the tumor area in units of pixels in each digital pathology image.

The method may further include: providing pathology analysis information for the prostatectomy specimen, in which the pathology analysis information may include the tumor burden, a tumor location, and the longest diameter of the tumor.

The providing the histological mapping image may include providing the histological mapping image through a digital pathology image viewer installed in a user terminal.

The method may further include: providing a digital pathology image and a histological mapping image generated from the same section on one screen through the digital pathology image viewer.

The method may further include standardizing the received digital slide image by a specified method and then inputting the standardized digital slide image into the artificial neural network model.

The prostate cancer-related histological information inferred from the artificial neural network model may include a tumor region, and the tumor region may be displayed as a contour and/or a heatmap in the corresponding digital slide image.

The artificial neural network model may be trained using digital slide images produced from prostatectomy specimens of various institutions.

Another embodiment of the present disclosure provides a method of operating an apparatus for prostate cancer analysis operated by at least one processor, the method comprising: receiving digital slide images produced from serial sections of a prostatectomy specimen; inferring a tumor region from each received digital slide image using an artificial neural network model trained to infer histological information from the digital slide images; and calculating a tissue area and a tumor area of the corresponding section based on the tumor region inferred from each digital slide image, and calculating a tumor burden which is a ratio of a total tumor area to a total tissue area calculated from the serial sections.

The calculating of the tumor burden may include: generating digital pathology images by displaying the tumor region inferred from the artificial neural network model on each digital slide image; calculating the tissue area and the tumor area in each digital pathology image; and calculating the tumor burden based on the total tissue area and the total tumor area calculated in the whole digital pathology image.

The calculating of the tissue area and the tumor area may include calculating the tumor area and the tumor area in units of pixels in each digital pathology image.

The method may further include: providing pathology analysis information for the prostatectomy specimen, in which the pathology analysis information may include the tumor burden, a tumor location, and the longest diameter of the tumor.

The method may further include generating a histological mapping image in which the tumor region extracted from each digital pathology image is mapped to a gross image of the corresponding section.

The generating the histological mapping image may include generating digital pathology images by displaying the tumor region inferred from the artificial neural network model on each digital slide image; extracting a tumor region from each digital pathology image, and generating histological mapping information for mapping the extracted tumor region to the gross image of the corresponding section; and generating the histological mapping image by applying the histological mapping information to the corresponding gross image.

The method may further include providing a digital pathology image and a histological mapping image generated from the same section on one screen through the digital pathology image viewer.

Yet another embodiment of the present disclosure provides an apparatus for prostate cancer analysis operated by at least one processor, including: an artificial neural network model that infers histological information from digital slide images produced from serial sections of a prostatectomy specimen, and a digital pathology image viewer that displays digital pathology images including prostate cancer-related histological information inferred from the artificial neural network model, and a histological mapping image in which a tumor region extracted from each digital pathology image is mapped to the corresponding gross image.

The digital pathology image viewer may display an interface screen capable of checking, modifying, or confirming histological information inferred from the artificial intelligence model.

The digital pathology image viewer may display a tumor burden of the prostatectomy specimen, and the tumor burden may be calculated based on a tissue area and a tumor area calculated from the digital pathology images.

According to an embodiment of the present disclosure, it is possible to determine whether or not prostate cancer is present not only in a biopsy but also in the whole resected prostate.

According to an embodiment of the present disclosure, it is possible to shorten screening time at the pathology practice, and improve diagnosis capability of a pathologist.

According to an embodiment of the present disclosure, since histological information is obtained using a digital pathology image and an artificial intelligence model produced in a standard way, it is possible to provide numeric value of tumor burden that is not affected by the interpretator's subjectivity and manual estimation.

According to an embodiment of the present disclosure, it is possible to improve cumbersomeness and inaccuracy of the conventional histological mapping operation by mapping a digital tumor region to a gross image.

DETAILED DESCRIPTION OF THE EMBODIMENTS

Figure 1:
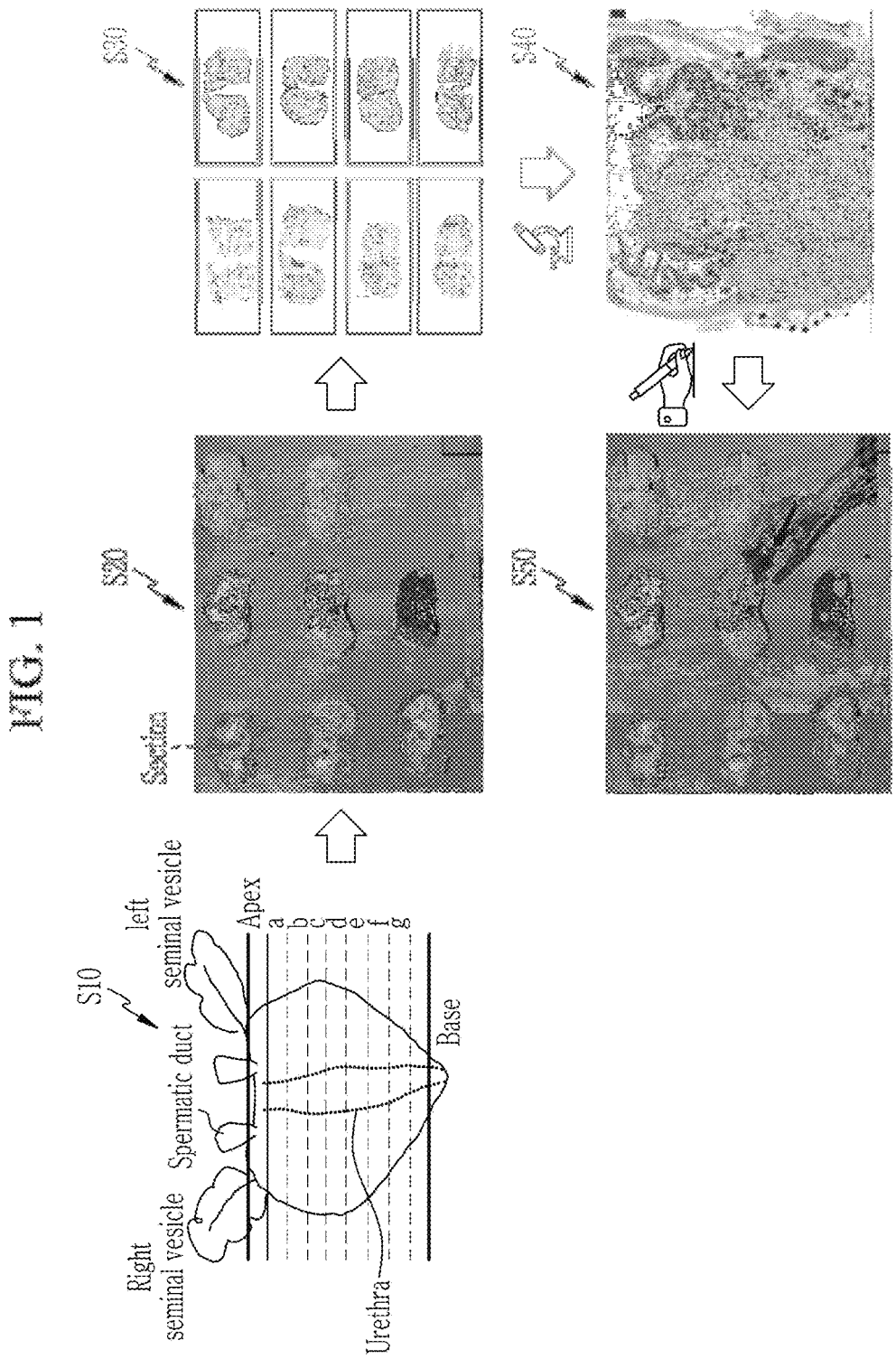
FIG. 1 is a diagram for describing a pathological inspection method for a conventional prostatectomy specimen.

Hereinafter, several exemplary embodiments of the present disclosure will be described in detail with reference to the accompanying drawings so that those skilled in the art to which the present disclosure pertains may easily practice the present disclosure. However, the present disclosure may be implemented in various different forms and is not limited to exemplary embodiments described herein. In addition, components unrelated to a description will be omitted in the accompanying drawings in order to clearly describe the present disclosure, and similar reference numerals will be used to denote similar components throughout the present specification.

Throughout the specification, unless explicitly described to the contrary, the word "comprise" and variations such as "comprises" or "comprising", will be understood to imply the inclusion of stated elements but not the exclusion of any other elements. In addition, the terms "-er", "-or", and "module" described in the specification mean units for processing at least one function and operation, and can be implemented by hardware components or software components, and combinations thereof.

FIG. 1 is a diagram for describing a pathological inspection method for a conventional prostatectomy specimen.

Referring to FIG. 1, a pathological inspection of a prostatectomy specimen is somewhat different for each institution, but the inspection institutions generally serially resection a surgically resected prostate from top to bottom or from front to rear at regular intervals (for example, 3-4 mm intervals) (S10).

The inspection agency takes pictures of serial sections of the resected prostate, and generates a gross image (S20).

The inspection institution manufactures serial sections with paraffin blocks, manufactures glass slides on which the paraffin blocks are placed (S30), and then inspects each glass slide with a microscope to check a tumor (S40). In this case, the inspection institution may draw an approximate boundary of the tumor checked with a microscope on a glass slide with a pen. Regarding prostate cancer, tumors are often not checked by a naked eye inspection, so a method of performing a microscopic inspection of the whole prostate using the paraffin block and the glass slide is used. For the microscopic inspection of the whole prostate, since the whole prostate is made of the glass slide, the glass slide ranges from at least 20 to 50 sheets per patient.

When the whole prostate is made of a glass slide, the inspection institution performs a histological inspection by manually displaying a tumor region confirmed with a microscope on a gross image (S50). The inspection institution may perform histological mapping by placing the glass slide, on which the tumor region is displayed, on the gross image, and then displaying the tumor region with a pen. An image in which the tumor region is displayed on the gross image may be called a histological mapping image.

As such, the histological mapping image visually provides information (left and right locations, the number, vertical lengths, maximum cross-sections of tumors, etc.) about tumors that are not checked with naked eye, and may estimate the location of tumor, the size of tumor, the distance from the closest surgical margins, a location where an invasion range is deepest, etc. Here, the distance from the closest cutting surface means the shortest distance from a tumor to a surface of the surgically removed prostate tissue. The state of the cutting surface may be used as a basis for determining whether cancer has invaded or how far the cutting surface is from the cancer.

However, since all sections of the whole prostate have to be microscopically inspected and the tumor region manually displayed on the glass slide should be transferred to a gross image, a pathological inspection procedure is very inconvenient, inaccurate, and affected by the subjectivity and manual estimation of a specialist.

Meanwhile, it is practically almost impossible to measure an exact size of a tumor in three dimensions or to quantify the tumor in an actual volume. Therefore, it is required to designate a tumor burden as a mandatory reporting item in a tissue pathological inspection report of prostate cancer, and to report the tumor burden between 1 and 100% based on normal tissue. However, although it is an important tumor burden for diagnosis and prognosis prediction of prostate cancer, there is a problem in that there is no standardized burden evaluation method, and a value varies greatly depending on the subjective evaluation of a specialist. As a result, there is a difference in the relationship between the tumor burden and prognosis of prostate cancer in various studies.

In the following, an apparatus and program for prostate cancer analysis based on an artificial intelligence model for solving this problem, and an operation method thereof will be described in detail.

Figure 2:
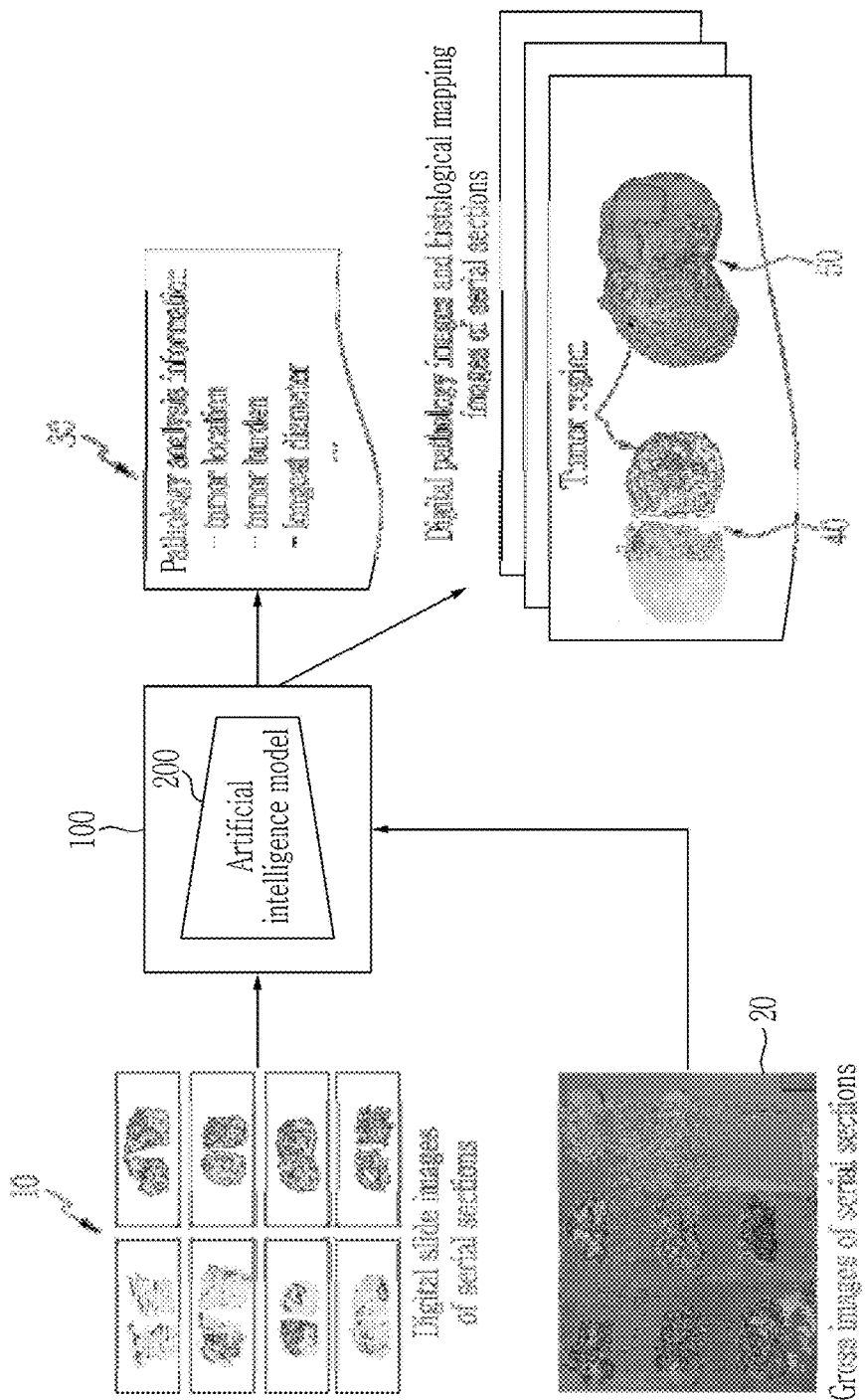
FIG. 2 is a diagram for describing an apparatus for prostate cancer analysis according to an exemplary embodiment.

FIG. 2 is a diagram for describing an apparatus for prostate cancer analysis according to an exemplary embodiment.

Referring to FIG. 2, an apparatus 100 for prostate cancer analysis operated by at least one processor acquires histological information used for prostate cancer screening by using an artificial intelligence model 200 trained to infer the histological information from digital slide images of prostate sections. In addition, the apparatus 100 for prostate cancer analysis may histologically map the tumor region inferred from the artificial intelligence model 200 to the gross image, calculate the tumor burden, and provide various types of information for prostate cancer diagnosis assistance on an interface screen.

The apparatus 100 for prostate cancer analysis may be implemented as a computing device equipped with a program for performing the present disclosure and hardware for executing the same, and may be, for example, a laptop computer, a server, etc. The computing device may operate as the apparatus 100 for prostate cancer analysis by installing and executing a program for performing the present disclosure. The apparatus 100 for prostate cancer analysis may operate individually at various local sites, and may interwork with a server (not illustrated) as necessary. Alternatively, some functions of the apparatus 100 for prostate cancer analysis may be built in the server, and some other functions (e.g., digital pathology image viewer) may be built in at least one local client (not illustrated), and the server and the client may be connected through a network.

The apparatus 100 for prostate cancer analysis based on a server may be connected to local clients through a network, and may receive an analysis request for digital slide images from the local clients. The apparatus 100 for prostate cancer analysis based on a server may provide an analysis result to a local client through a digital pathology image viewer. The apparatus 100 for prostate cancer analysis based on a server may support image formats supported by various types of scanners, and standardize digital slide images produced in various forms by a specified method, and then input the standardized digital slide images to the artificial intelligence model 200.

The apparatus 100 for prostate cancer analysis may receive digital slide images 10 produced from serial sections of a prostatectomy specimen and a gross image 20 of the serial sections, and may provide analysis results. The analysis result may include pathology analysis information 30, a digital pathology image 40 for serial sections, and a histological mapping image 50. The pathology analysis information 30 may include histological information (whether there is a tumor, tumor region, etc.) inferred from the artificial intelligence model 200, a tumor burden analyzed based on the information, the longest diameter, etc. The tumor burden is a ratio of cancer to the prostate tissue, and longest diameter is the longest cross-sectional size in the tumor. The pathology analysis information 30 may further include a tissue area and a tumor area used to calculate the tumor burden. The pathology analysis information 30 may include detailed analysis information for each digital slide image, and include comprehensive analysis information thereof.

The apparatus 100 for prostate cancer analysis may visually provide an analysis result through a digital pathology image viewer that provides interaction with a user. The apparatus 100 for prostate cancer analysis may shorten the cancer screening time at pathology unit, increase diagnosis accuracy, and improve diagnosis capability of a pathologist.

The digital slide images 10 are images obtained by converting glass slides of serial sections into digital images. A method of converting a glass slide into a digital image may be a whole slide imaging (WSI) method of digitizing a part or all of contents of a glass slide by scanning a part or all of the contents of the glass slide at a high magnification.

The gross image 20 is a photographic image of serial sections. The gross image 20 may be photographed for each section, or may be photographed to include the whole section.

The apparatus 100 for prostate cancer analysis may manage the sections included in the digital slide images 10 and the sections of the gross image 20 to correspond to each other. The apparatus 100 for prostate cancer analysis may manage the corresponding sections to have the same index. The index assignment method may vary, and may be sequentially assigned according to the order and direction (left and right or up and down) in which the prostate is sectioned at regular intervals.

The apparatus 100 for prostate cancer analysis acquires histological information inferred from the digital slide images 10 produced from prostate sections through the artificial intelligence model 200. The histological information may include various types of pathological information such as whether there is a tumor inferred from each digital slide image and a tumor region. The artificial intelligence model 200 may determine whether there is a tumor in units of pixels, and the pixels determined as a tumor form a tumor region. The apparatus 100 for prostate cancer analysis may standardize the input digital slide images by the specified method, and then input the standardized input digital slide images to the artificial intelligence model 200. Contrast, color, size, etc. of the digital slide images may be standardized.

The apparatus 100 for prostate cancer analysis may extract pathology analysis information 30 such as the tumor location, the tumor burden, and the longest diameter of the tumor based on various types of histological information such as the tumor region inferred from the artificial intelligence model 200.

The apparatus 100 for prostate cancer analysis may generate N pathology analysis information files corresponding to N digital slide images. The pathology analysis information file may be modified by the user in the digital pathology image viewer.

The apparatus 100 for prostate cancer analysis may provide a digital pathology image 40 in which the tumor region is visually displayed on a digital slide image. For example, the tumor region may be displayed as a contour or a heatmap. The prostate cancer analysis apparatus 100 may fetch the histological information (tumor region) included in the pathology analysis information file and provide the digital pathology image 40 to be displayed on the digital slide image.

The apparatus 100 for prostate cancer analysis may calculate a tissue area and a tumor area in each digital pathology image 40, and determine a ratio of a total tumor area to a total tissue area as a tumor burden. A method of calculating an area in each digital pathology image 40 may vary, but the area may be calculated in units of pixels.

The apparatus 100 for prostate cancer analysis may map the tumor region of the corresponding section to the gross image 20 of each section. The apparatus 100 for prostate cancer analysis extracts a tumor region from each digital pathology image 40 and generates histological mapping information for mapping the tumor region to the gross image 20. The image in which the tumor region is mapped to the gross image may be referred to as the histological mapping image 50. During the histological mapping, the size/shape of the tissue region included in the digital pathology image 40 and the tissue region of the gross image may be different. Accordingly, the apparatus 100 for prostate cancer analysis corrects the magnification of the digital pathology image so that the tissue region of the digital pathology image 40 matches the actual tissue region of the gross image. The apparatus 100 for prostate cancer analysis adjusts the size of the tumor region of the digital pathology image 40 according to the correction magnification, and stores the size-adjusted tumor area location mapped to the gross image as the histological mapping information. By applying the histological mapping information to the gross image, it is possible to generate a histological mapping image 50 in which the tumor region is displayed.

The apparatus 100 for prostate cancer analysis may provide the digital pathology image 40 in which the histological information is displayed (e.g., overlaid) on the digital slide image through the digital pathology image viewer, and may provide the mapping image 50 in which the histological information is displayed (e.g., overlaid) on the gross image. In this case, the apparatus 100 for prostate cancer analysis may provide the digital pathology image 40 and the histological mapping image 50 matched to each other on one screen, so a pathologist may simultaneously check the images.

The apparatus 100 for prostate cancer analysis may confirm pathology analysis information after checking or modifying the inference result of the artificial intelligence model 200 for the digital slide images 10 by a specialist. That is, when the pathologist checks or modifies the inference results of the artificial intelligence model 200 to confirm the tumor region, the confirmed tumor region is reflected in the pathology analysis information file. The apparatus 100 for prostate cancer analysis may provide the digital pathology image 40 based on the histological information confirmed by a pathologist, provide the histological mapping image 50 based on the tumor region of the digital pathology image 40, and provide the pathology analysis information including the tumor burden.

Figure 3:
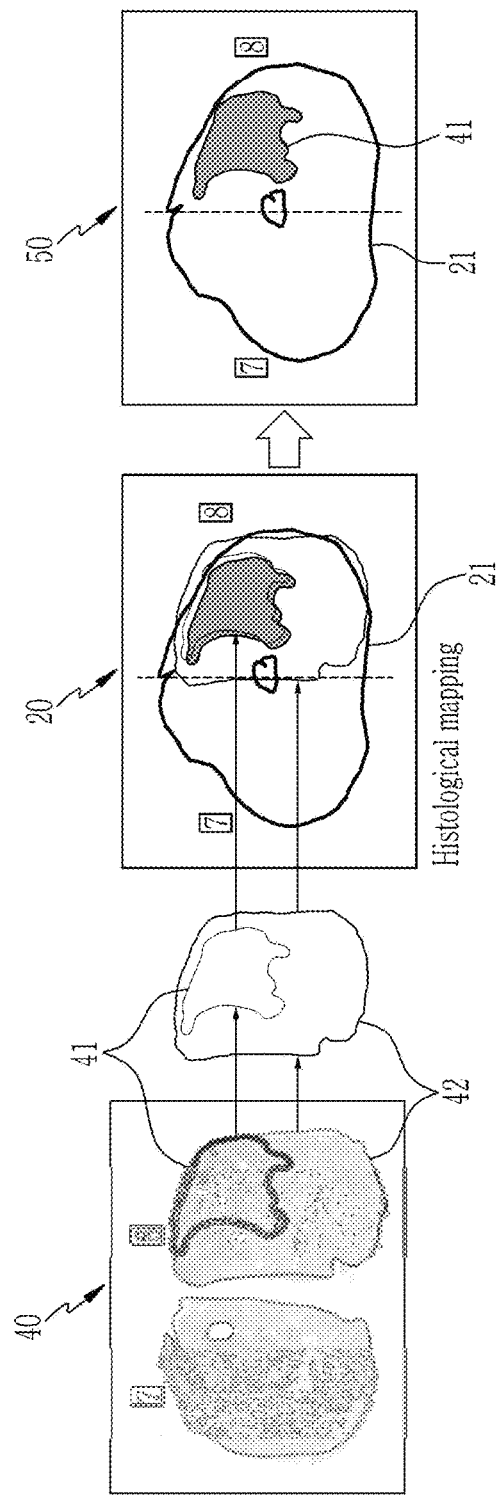
FIG. 3 is a diagram for describing histological mapping according to an exemplary embodiment.
Figure 4:
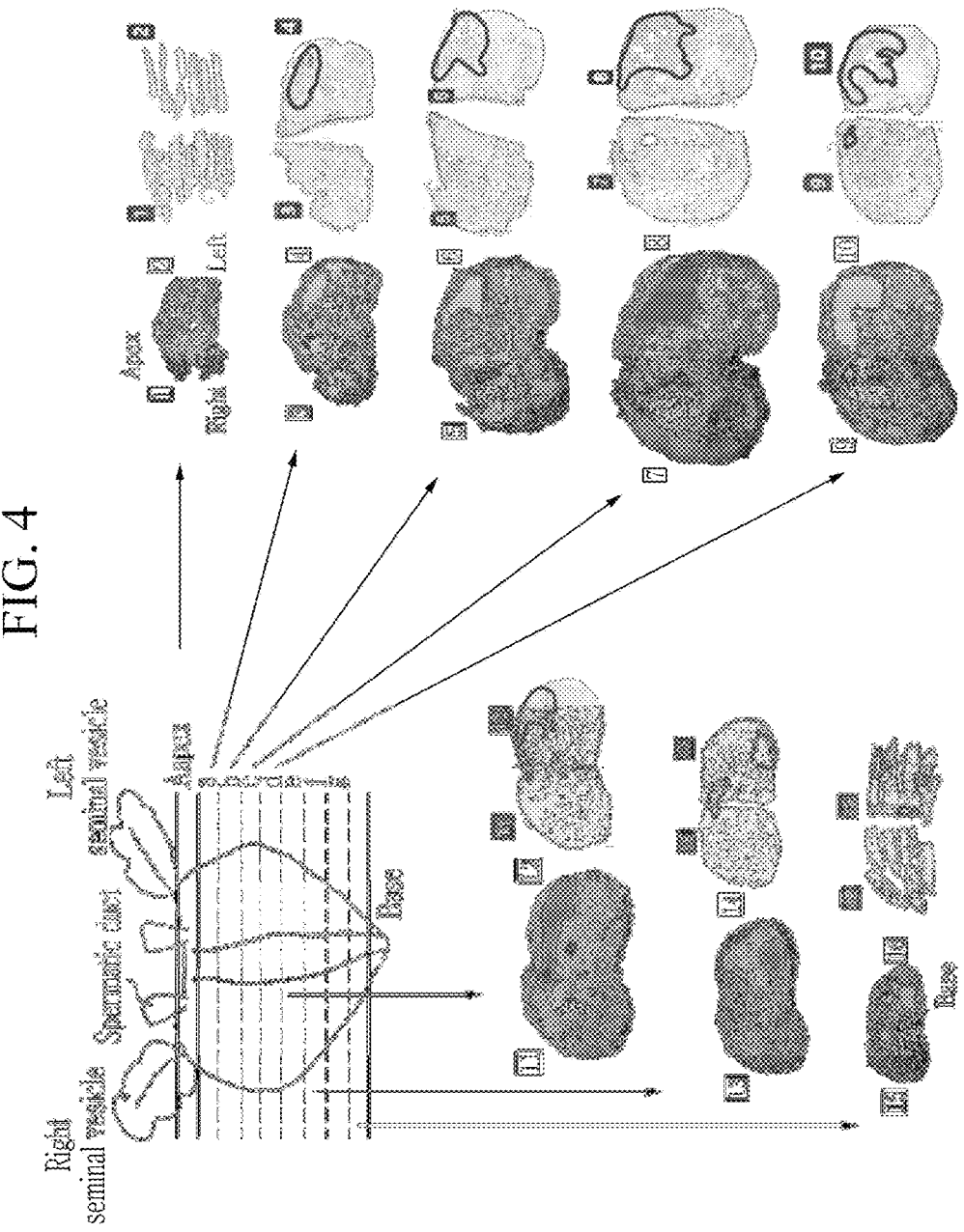
FIG. 4 is a diagram for describing a histological mapping result of a prostatectomy specimen according to an exemplary embodiment.

FIG. 3 is a diagram for describing histological mapping according to an exemplary embodiment, and FIG. 4 is a diagram for describing a histological mapping result of a prostatectomy specimen according to an exemplary embodiment.

Referring to FIG. 3, the apparatus 100 for prostate cancer analysis may extract the tumor margin (region boundary) 41 when a tumor is present in the digital pathology image 40 of a certain section. The apparatus 100 for prostate cancer analysis may map the tumor margin 41 to the gross image 20 in which the photographed actual tissue 21 is displayed. For example, the apparatus 100 for prostate cancer analysis may map a tumor region to a gross image of index 8 when a tumor exists in a tissue of the index 8. The term of margin means the edge or border in the pathology.

The apparatus 100 for prostate cancer analysis may match a tissue margin 42 extracted from the digital pathology image 40 to a tissue 21 of the gross image 20 to overlay the tumor margin 41 with the tissue 21 of the gross image 20.

Meanwhile, during the histological mapping, the size/shape/direction of the tissue region included in the digital pathology image 40 and the tissue region of the gross image may be different. Therefore, the apparatus 100 for prostate cancer analysis may extract the tissue margin 42 from the digital pathology image 40, and the correction magnification of the digital pathology image in which the normal tissue margin 42 matches the tissue 21 of the gross image 20 may be determined. The apparatus 100 for prostate cancer analysis may generate the histological mapping image 50 in which the digital tumor margin 41 is mapped to the photographed tissue 21.

Referring to FIG. 4, a prostatectomy specimen may be serially sectioned at regular intervals from an apex to a base. Serial sections may include a leading section, section a, section b, section c, section d, section e, and section f, and a base section, and sequential indexes may be assigned to the left and right of each section.

The apparatus 100 for prostate cancer analysis may generate histological mapping (left) by determining the tumor region from the digital pathology image (right) of each section through the artificial intelligence model 200, and mapping the determined tumor region to the gross image photographed of the corresponding section.

The apparatus 100 for prostate cancer analysis may simultaneously provide mutually matched digital pathology images and histological mapping images. Accordingly, the pathologist may confirm the tumor information determined from the digital slide image and the location, size, etc., of the tumor in the actual tissue, thereby making an accurate diagnosis.

Figure 5:
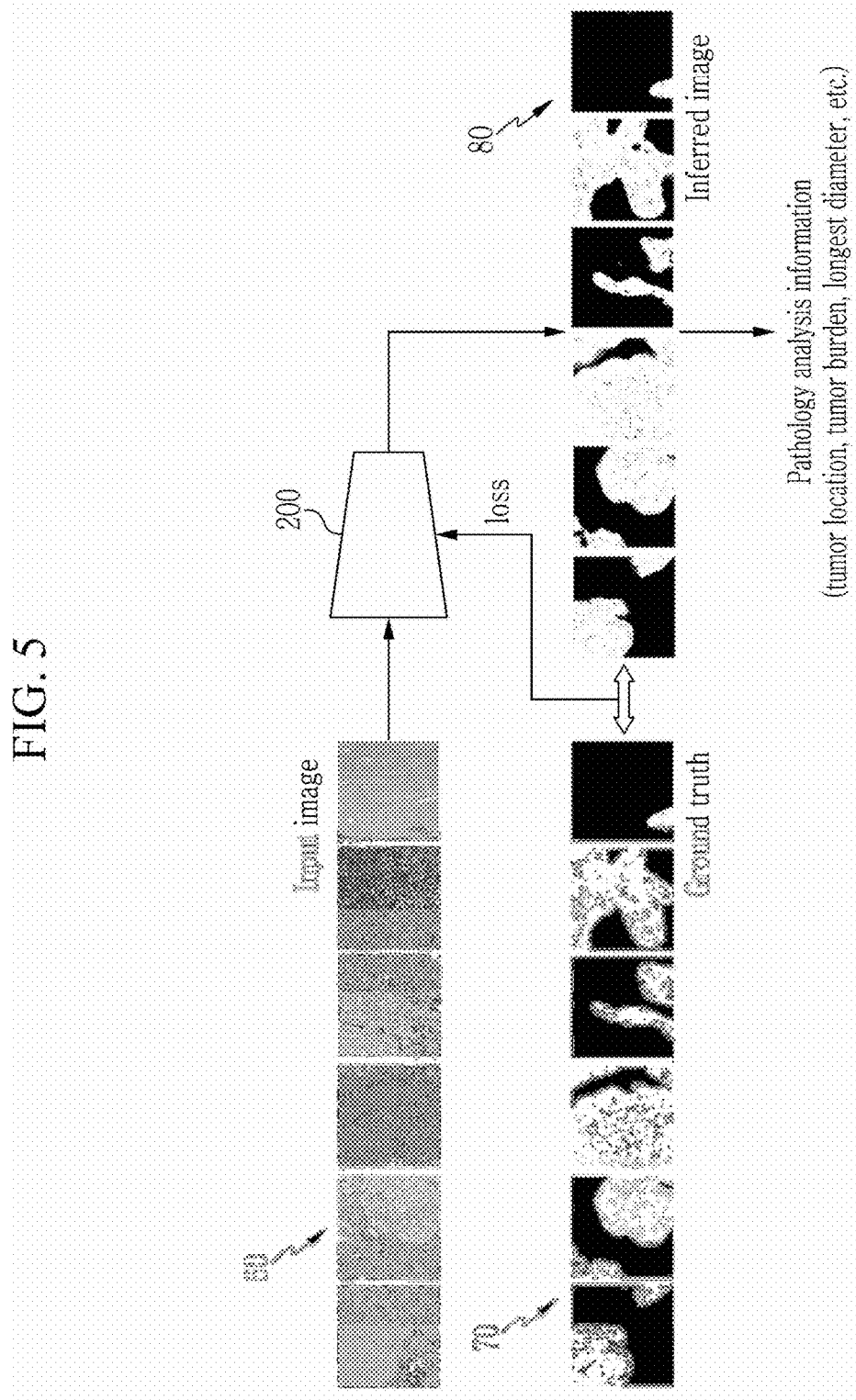
FIG. 5 is a diagram schematically illustrating artificial intelligence model learning according to an exemplary embodiment.
Figure 6:
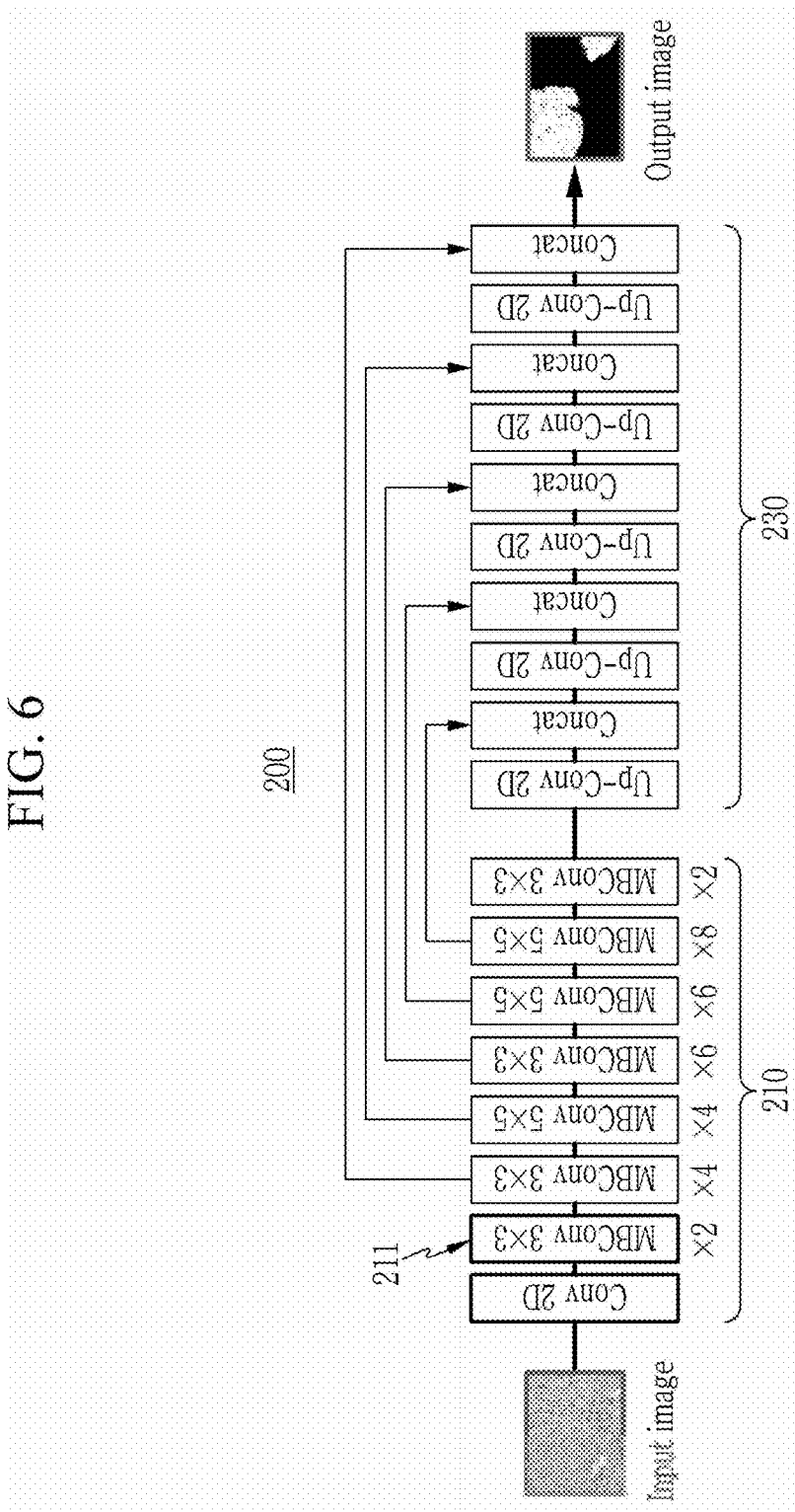
FIG. 6 is a diagram illustrating a network structure of an artificial intelligence model according to an exemplary embodiment.

FIG. 5 is a diagram for schematically describing artificial intelligence model learning according to an exemplary embodiment, and FIG. 6 is a network structure of an artificial intelligence model according to an exemplary embodiment.

Referring to FIG. 5, the artificial intelligence model 200 is trained to infer the histological information from the digital slide images produced as serial sections of a prostatectomy specimen. The pathology analysis information such as the tumor location, the tumor burden, and the longest diameter of the tumor may be extracted based on the histological information, such as whether there is the tumor and the tumor region, inferred from the artificial intelligence model 200.

The training data may vary according to a structure, a training method, a task, etc., of the artificial intelligence model 200. For example, when the artificial intelligence model 200 is supervised to discriminate a tumor from an input, the training data may include digital slide images 60 produced as serial sections of a prostatectomy specimen and a ground truth image 70 of the digital slide images 60. The ground truth images 70 may be produced based on images in which a tumor region is annotated on digital slide images 60.

The artificial intelligence model 200 may be trained by a training device (not illustrated). The artificial intelligence model 200 performs training while adjusting network parameters in a direction in which a loss between the image 80 inferred from the input digital slide image 60 and the ground truth image 70 is reduced. In this case, the artificial intelligence model 200 may receive the whole digital slide image, and may receive a partial digital slide image fragmented into a patch.

The digital slide images 60 for training may be images in which contrast, color, size, etc., are standardized. In order to prevent the training bias of the artificial intelligence model 200, the digital slide images 60 produced from the prostatectomy specimens of various institutions may be used for training.

Meanwhile, when the number of patches including normal cells and the number of patches including abnormal cells (cancer cells) are not uniform, it is difficult for the artificial intelligence model 200 to predict a class to which a minority patch belongs due to the training bias. Therefore, the training data is prepared to maintain data balancing so that the training of the artificial intelligence model 200 is not focused on a specific classification class. For example, based on the training results for each ratio of a patch including normal cells and a patch including abnormal cells (a patch in which a cancer cell area is 20% or more), a ratio of 1:1 that showed the best results may be found, and the training data may be produced at a uniform ratio.

The training data may be increased through random left-right inversion, cropping, color jitter, and normalization.

A human-in-the-loop CNN model learning technique may be used to train the artificial intelligence model 200. Specifically, the artificial intelligence model may perform initial supervised learning based on a dataset of a first institution annotated with a discriminant label, or perform semi-supervised learning by adding a dataset without annotations of a first institution and new institutions. Thereafter, the inference results for the dataset of the existing first institution and the dataset of the new institutions are obtained by using the initially trained artificial intelligence model. Based on the inference results acquired from the artificial intelligence model, the labels of the dataset of the existing first institution and the dataset of the new institutions are modified. Thereafter, the artificial intelligence model may be further trained by using all the datasets annotated with the modified label. Through this, network performance may be improved, and the annotation cost of a pathologist may be reduced.

Referring to FIG. 6, the artificial intelligence model 200 may be implemented in various network structures. For example, the artificial intelligence model 200 may include an encoder 210 and a decoder 230, and may be implemented based on U-Net that is restored with reference to the encoded features.

The encoder 210 has a network structure for extracting features from an input image. The encoder 210 may be implemented as a network structure, for example, EfficientNet capable of determining the presence or absence of prostate cancer in units of pixels for diagnosing prostate cancer assistance.

The encoder 210 may include sequential mobile inverted bottleneck convolution (MBConv) blocks 211. Each MBConv block may include a depthwise convolution and a squeeze-and excitation network (SENet).

The decoder 230 has a network structure for restoring the features of the input image extracted by the encoder 210. The decoder 230 may reconstruct with reference to features extracted from the MBConv blocks of the encoder 210.

The existing prostate cancer pathology factor inference using a machine learning-based deep neural network (DNN) provides performance of 77.3% to 79.6% based on mean intersection over union (mIoU), and the prostate cancer pathology factor inference of the artificial intelligence model 200 may provide performance of more than 92.9% based on mIoU.

Figure 7:
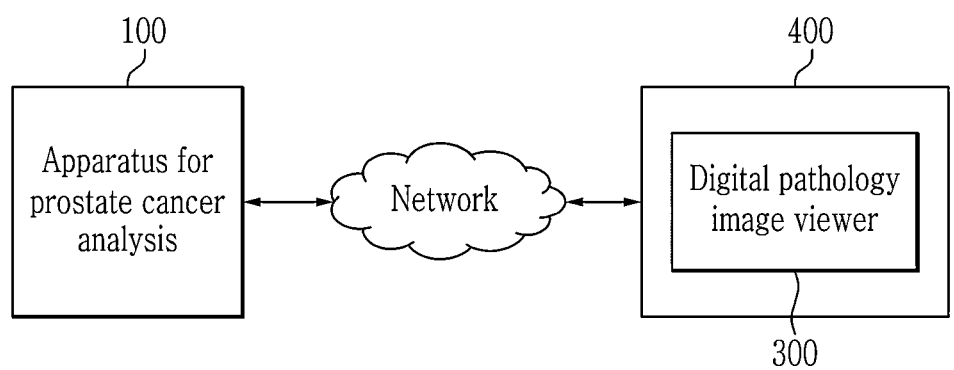
FIG. 7 is a diagram for describing a digital pathology image viewer according to an exemplary embodiment.
Figure 8:
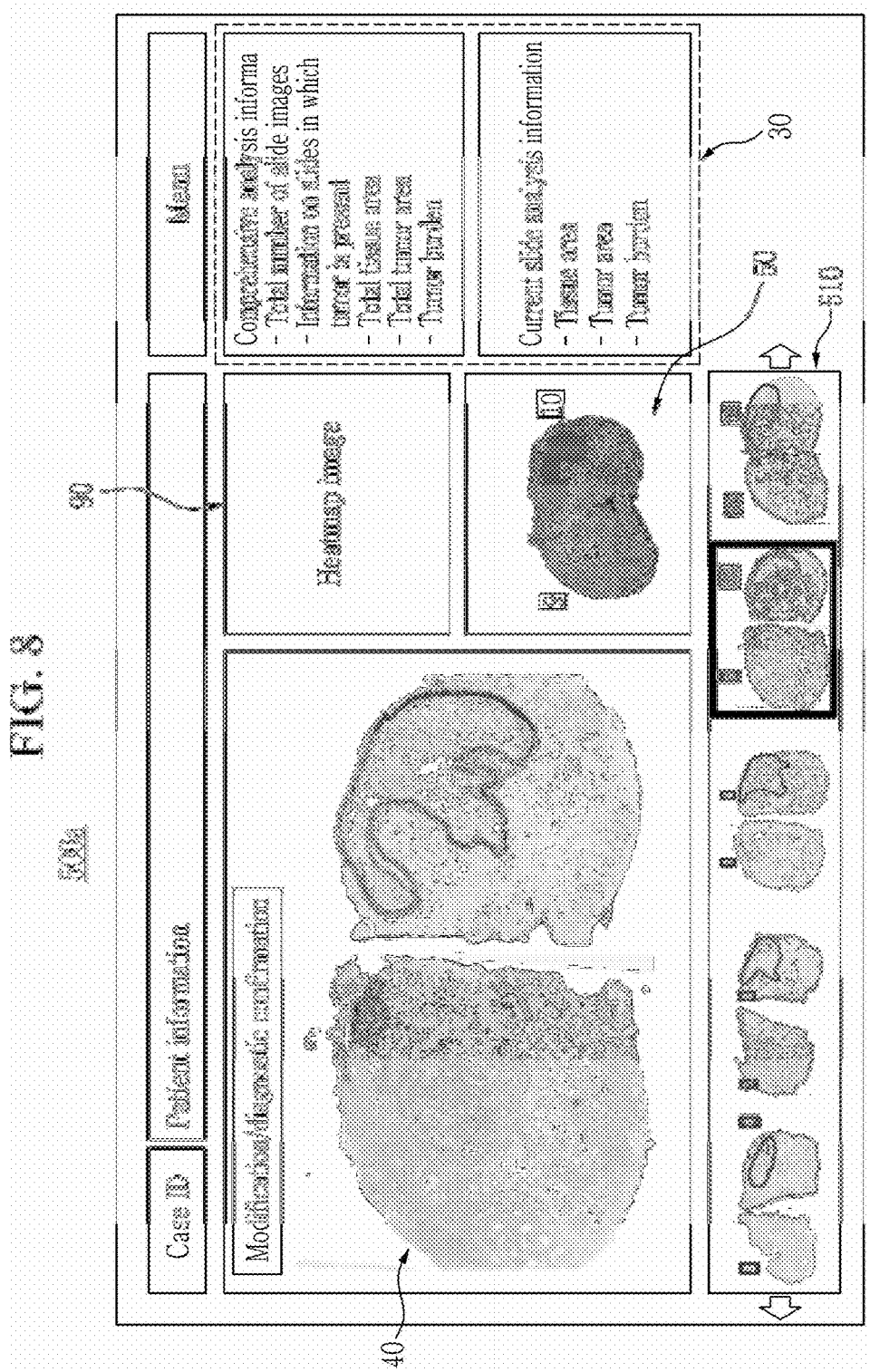
FIGS. 8 and 9 are examples of an interface screen of the digital pathology image viewer according to the exemplary embodiment.
Figure 9:
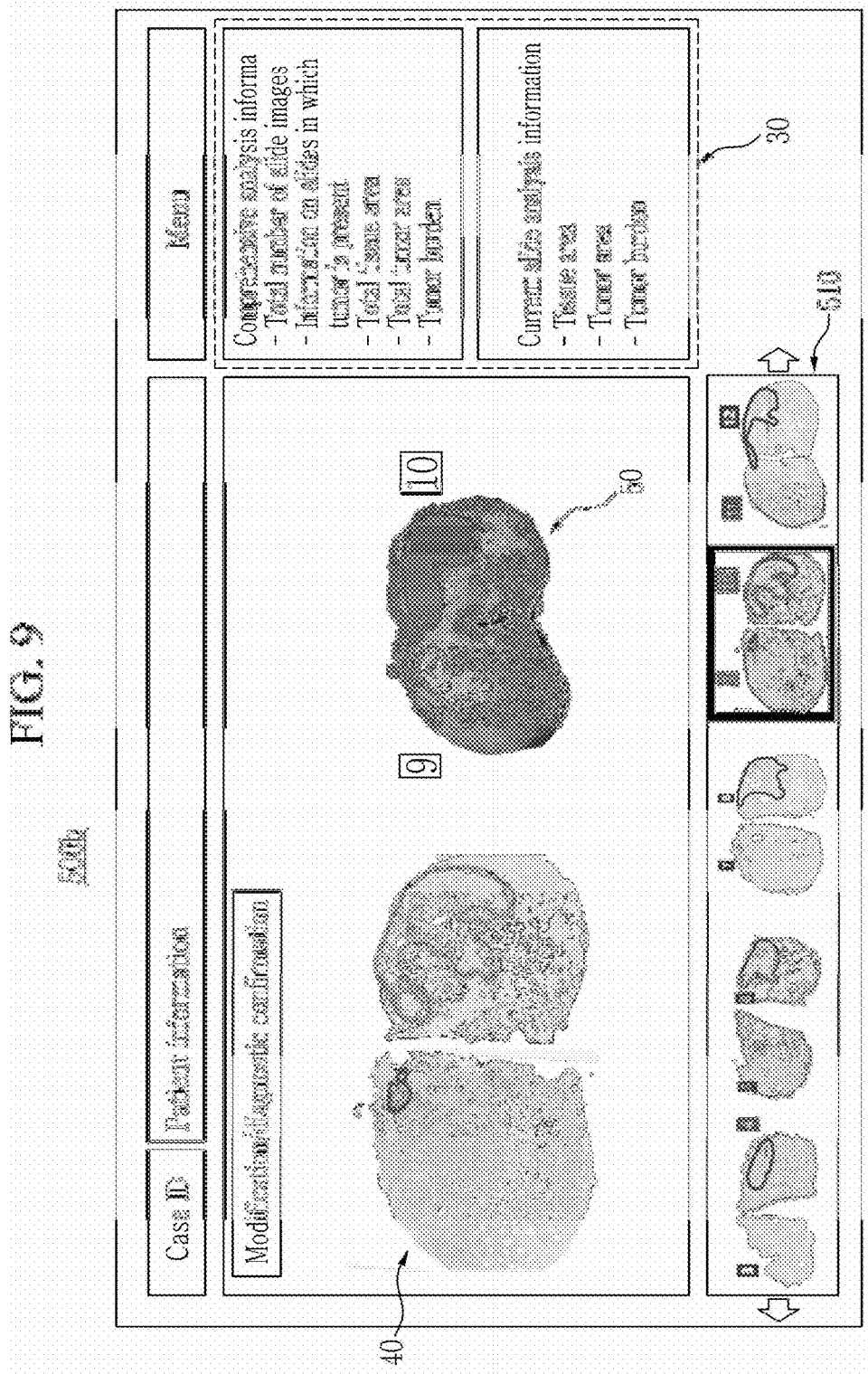

FIG. 7 is a diagram for describing a digital pathology image viewer according to an exemplary embodiment, and FIGS. 8 and 9 are examples of interface screens of the digital pathology image viewer according to the exemplary embodiment.

Referring to FIG. 7, the apparatus 100 for prostate cancer analysis may visually provide an analysis result for a prostatectomy specimen through a digital pathology image viewer 300. The digital pathology image viewer 300 is a program installed in a user terminal 400 and may access the apparatus 100 for prostate cancer analysis through a network.

The apparatus 100 for prostate cancer analysis may manage digital slide images, histological information of each digital slide image, gross images, histological mapping information, and pathology analysis information (tumor location, tumor burden, the longest diameter, etc.) for each patient. Here, patient images such as digital slide images and gross images may be managed in a separate image management system, but for convenience of explanation, it is assumed that the apparatus 100 for prostate cancer analysis may be connected with the digital pathology image viewer 300 through the network. Meanwhile, according to the patient data management policy, at least some patient data managed in the apparatus 100 for prostate cancer analysis may be stored in the user terminal 400.

The digital pathology image viewer 300 may visually display information provided by the apparatus 100 for prostate cancer analysis on the display device of the user terminal 400, and a screen layout and function may be designed in various ways.

The digital pathology image viewer 300 may provide an image enlargement/reduction/movement function, a multi-view function for simultaneously inquiring multiple images by splitting the screen, a navigation function between images, and the like.

The digital pathology image viewer 300 may provide an interface screen through which a pathologist may check, correct, or confirm the inference result of the artificial intelligence model 200. The digital pathology image viewer 300 may provide an interface screen for a user to edit the tumor region displayed as a contour, a heatmap, or the like, and transmit the tumor region modified by the user (pathologist) to the apparatus 100 for prostate cancer analysis, thereby updating the pathology analysis information. Here, the analysis result inferred from the artificial intelligence model 200 and the result updated by the user may be stored separately.

The digital pathology image viewer 300 may provide an interface screen that displays the digital slide image and gross image corresponding to each other together, or displays the digital pathology image and the histological mapping image together.

Referring to FIGS. 8 and 9, the digital pathology image viewer 300 may display interface screens 500*a* and 500*b* on the display device of the user terminal 400.

The interface screens 500*a* and 500*b* may display the digital pathology image 40 in which a tumor region is displayed as a contour or a heatmap on the digital slide image. The tumor region displayed by the contour, the heatmap, or the like may be modified by the user, and the pathology analysis information file may be updated with the modified tumor region.

The interface screens 500*a* and 500*b* may provide a menu 510 for selecting the digital slide image/digital pathology image/gross image.

The interface screens 500*a* and 500*b* may display the pathology analysis information 30 including current slide analysis information and comprehensive analysis information displayed on the current screen. The current slide analysis information may include, for example, a tissue area, a tumor area, a tumor burden, and the like, and the comprehensive analysis information may include the total number of digital slide images, the digital slide information in which a tumor is present, the total tissue area, the total tumor area, and the tumor burden, and the like.

The interface screens 500*a* and 500*b* may display the digital pathology image 40 and the histological mapping image 50 on one screen. In addition, a heatmap image 90 may be further displayed.

Figure 10:
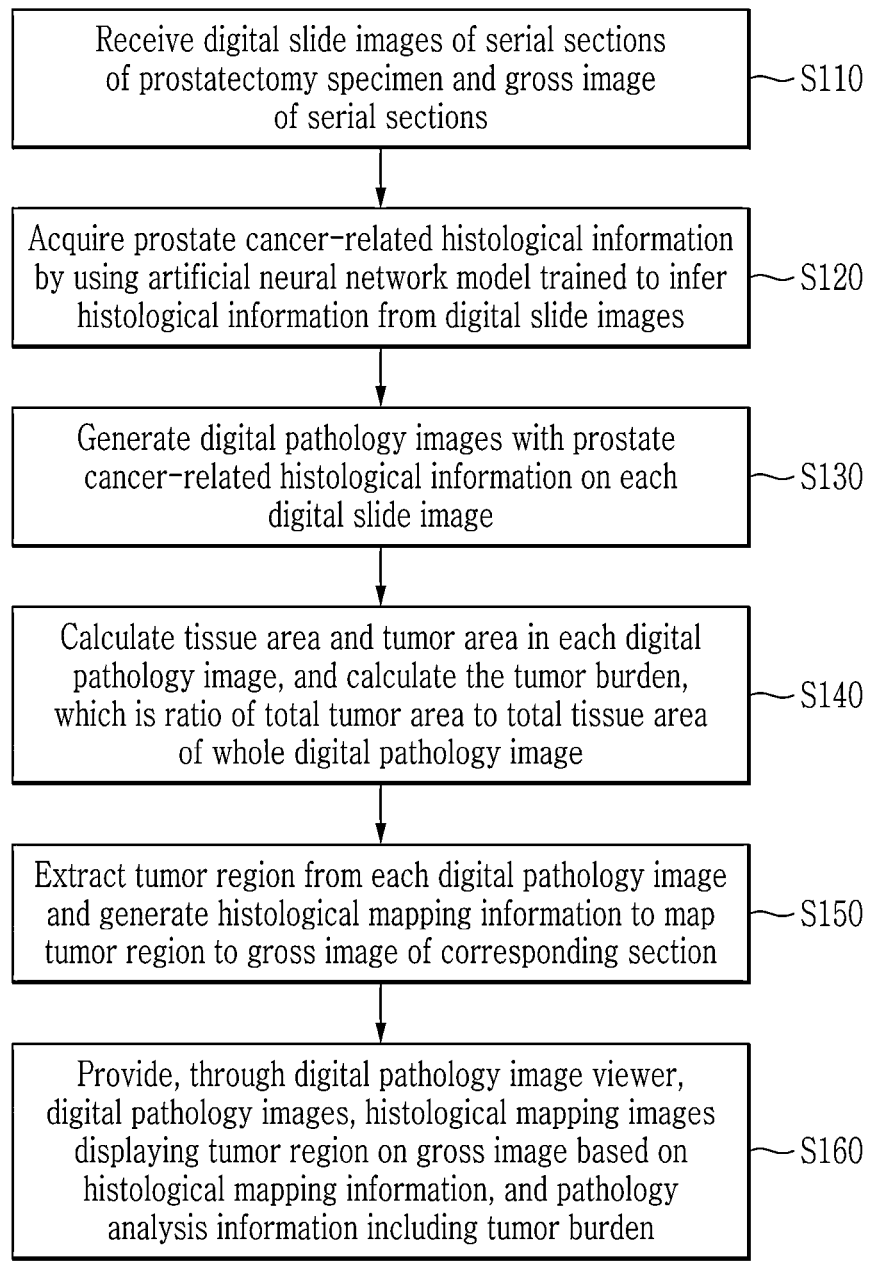
FIGS. 10 and 11 are flowcharts of a method for prostate cancer analysis according to an exemplary embodiment.
Figure 11:
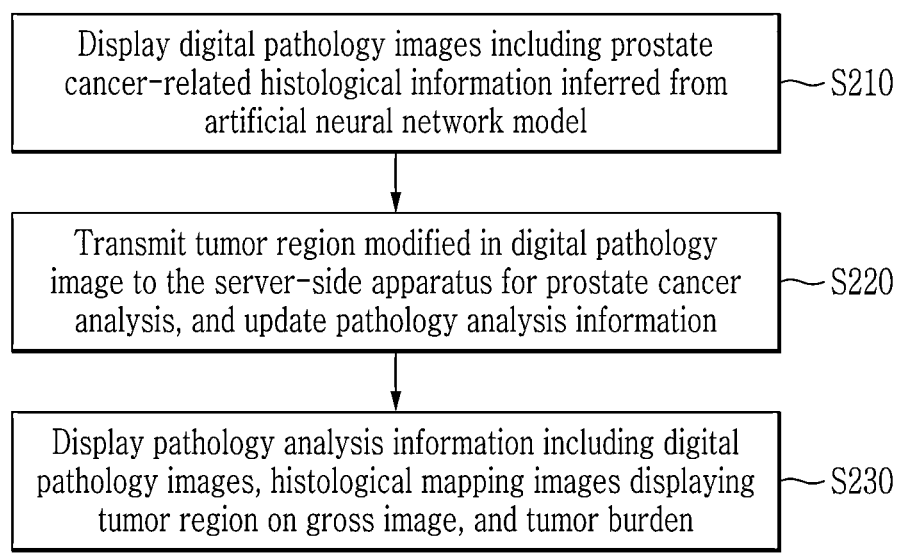

FIGS. 10 and 11 are flowcharts of a method for prostate cancer analysis according to an exemplary embodiment.

Referring to FIG. 10, the apparatus 100 for prostate cancer analysis receives digital slide images of serial sections of a prostatectomy specimen, and gross images of serial sections (S110). The digital slide images are images obtained by converting glass slides of serial sections into digital images. The apparatus 100 for prostate cancer analysis may perform analysis after standardizing digital slide images in a designated method (contrast, color, size, etc.).

The apparatus 100 for prostate cancer analysis acquires prostate cancer-related histological information by using the artificial intelligence model 200 trained to infer histological information from digital slide images (S120). The histological information may include whether there is a tumor, a tumor region, and the like. The artificial intelligence model 200 may determine whether a tumor is present in units of pixels of the digital slide image.

The apparatus 100 for prostate cancer analysis generates a digital pathology image in which prostate cancer-related histological information is displayed on each digital slide image (S130). The apparatus 100 for prostate cancer analysis may generate a digital pathology image in which the tumor region is displayed as a contour, a heatmap, or the like. The apparatus 100 for prostate cancer analysis may provide a digital pathology image through a digital pathology image viewer and update a pathology analysis information file to a tumor region modified by a user.

The apparatus 100 for prostate cancer analysis calculates a tissue area and a tumor area in each digital pathology image, and calculates a tumor burden, which is a ratio of the total tumor area to the total tissue area of the whole digital pathology image (S140). The apparatus 100 for prostate cancer analysis may calculate the area in units in pixels in each digital pathology image.

The apparatus 100 for prostate cancer analysis extracts a tumor region from each digital pathology image, and generates histological mapping information for mapping the tumor region to the gross image of the corresponding section (S150). The apparatus 100 for prostate cancer analysis may correct the magnification of the digital pathology image so that the tissue region of the digital pathology image matches the actual tissue region of the gross image, and adjust the size of the tumor region of the digital pathology image according to the correction magnification. The apparatus 100 for prostate cancer analysis may store the size-adjusted tumor region mapped to the gross image as the histological mapping information. The apparatus 100 for prostate cancer analysis may generate the histological mapping image in which the tumor region is displayed by applying the histological mapping information to the gross image.

The apparatus 100 for prostate cancer analysis provides pathology analysis information including the digital pathology images, the histological mapping images displaying the tumor region on the gross image based on the histological mapping information, and the tumor burden through the digital pathology image viewer (S160). The pathology analysis information may include the histological information (whether there is a tumor, the tumor region, etc.) inferred from the artificial intelligence model 200, the tumor burden analyzed based on the histological information, and the longest diameter. The pathology analysis information may further include a tissue area and a tumor area used to calculate the tumor burden. The pathology analysis information may include detailed analysis information for each digital slide image, and include comprehensive analysis information thereof.

Referring to FIG. 11, the digital pathology image viewer 300 may be installed in the user terminal 400, and may display the pathology analysis information on the screen in conjunction with the server-side apparatus 100 for prostate cancer analysis.

The digital pathology image viewer 300 displays digital pathology images including prostate cancer-related histological information inferred from the artificial neural network model (S210). The digital pathology images visually display prostate cancer histological information inferred from serial sections of the prostatectomy specimen.

The digital pathology image viewer 300 transmits the tumor region modified in the digital pathology image to the server-side apparatus 100 for prostate cancer analysis, and updates the pathology analysis information (S220).

The digital pathology image viewer 300 displays pathology analysis information including digital pathology images, histological mapping images displaying a tumor region on a gross image, and a tumor burden (S230). The histological mapping image is an image displaying the tumor region by applying the histological mapping information to the gross image. The histological mapping information may include the location of the tumor region displayed on the gross image. The pathology analysis information may include the histological information (whether there is a tumor, the tumor region, etc.) inferred from the artificial intelligence model 200, the tumor burden analyzed based on the histological information, and the longest diameter. The pathology analysis information may further include a tissue area and a tumor area used to calculate the tumor burden. The pathology analysis information may include detailed analysis information for each digital slide image, and include comprehensive analysis information thereof.

Figure 12:
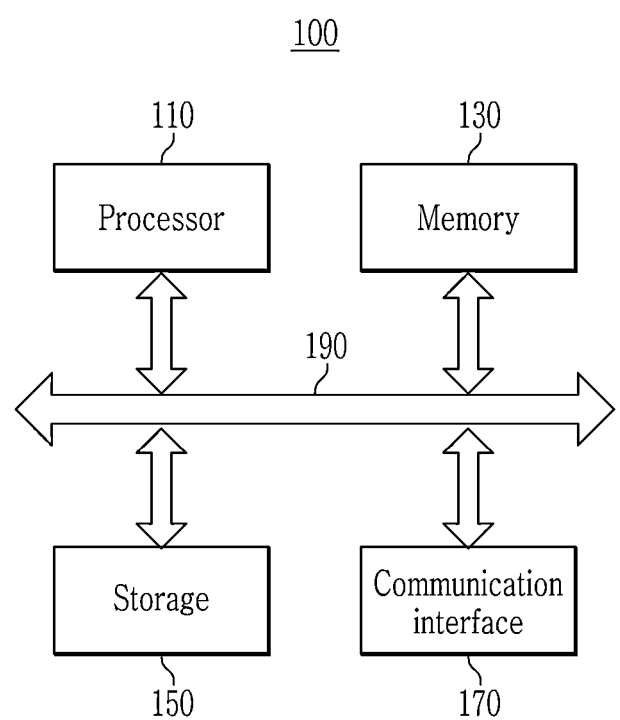
FIG. 12 is a hardware configuration diagram of an apparatus for prostate cancer analysis according to an exemplary embodiment.

FIG. 12 is a hardware configuration diagram of an apparatus for prostate cancer analysis according to an exemplary embodiment.

Referring to FIG. 12, the apparatus 100 for prostate cancer analysis may be implemented as a computing device operated by at least one processor. The apparatus 100 for prostate cancer analysis may include one or more processors 110, a memory 130 for loading a computer program performed by the processor 110, a storage device 150 for storing computer programs and various data, a communication interface 170, and a bus 190 connecting these components. In addition, the apparatus 100 for prostate cancer analysis may further include various components.

The processor 110 is a device for controlling an operation of the apparatus 100 for prostate cancer analysis, and may be various types of processors that process instructions included in a computer program, and may be configured to include at least one of, for example, a central processing unit (CPU), a microprocessor unit (MPU), a microcontroller unit (MCU), a graphic processing unit (GPU), or any type of processors well known in the art of the present disclosure.

The memory 130 stores various data, instructions, and/or information. The memory 130 may load the corresponding computer program from the storage device 150 so that the instructions described to execute the operations of the present disclosure are processed by the processor 110. The memory 130 may be, for example, read only memory (ROM), random access memory (RAM), or the like.

The storage device 150 may non-temporarily store computer programs and various data. The storage device 150 may be configured to include a nonvolatile memory, such as a read only memory (ROM), an erasable programmable ROM (EPROM), an electrically erasable programmable ROM (EEPROM), and a flash memory, a hard disk, a removable disk, or any well-known computer-readable recording medium in the art to which the present disclosure pertains.

The communication interface 170 may be a wired/wireless communication module supporting wired/wireless communication.

The bus 190 provides a communication function between components of the apparatus 100 for prostate cancer analysis.

The computer program includes instructions that are executed by the processor 110, and is stored in a non-transitory computer readable storage medium, in which the instructions allow the processor 110 to execute the operation of the present disclosure. The computer program may be downloaded over a network or sold as a product form. The artificial intelligence model 200 may be implemented as a computer program executed by the processor 110.

As described above, according to an embodiment of the present disclosure, it is possible to determine whether or not prostate cancer is present not only in a biopsy but also in the whole resected prostate.

According to an embodiment of the present disclosure, it is possible to shorten screening time at the pathology practice, and improve diagnosis capability of a pathologist.

According to an embodiment of the present disclosure, since histological information is obtained using a digital pathology image and an artificial intelligence model produced in a standard way, it is possible to provide numeric value of tumor burden that is not affected by the interpretator's subjectivity and manual estimation.

According to an embodiment of the present disclosure, it is possible to improve cumbersomeness and inaccuracy of the conventional histological mapping operation by mapping a digital tumor region to a gross image.

The exemplary embodiment of the present disclosure described above is not implemented only through the apparatus and method, and may be implemented through a program for realizing a function corresponding to the configuration of the exemplary embodiment of the present disclosure or a recording medium in which the program is recorded.

Although the exemplary embodiment of the present disclosure has been described in detail hereinabove, the scope of the present disclosure is not limited thereto. That is, several modifications and alterations made by a person of ordinary skill in the art using a basic concept of the present disclosure as defined in the claims fall within the scope of the present disclosure.

What is claimed is:

1. A method of operating an apparatus for prostate cancer analysis operated by at least one processor, the method comprising:
   receiving digital slide images prepared from serial sections of a prostatectomy specimen, and a gross image of the serial sections;
   acquiring prostate cancer-related histological information of each received digital slide image, using an artificial neural network model trained to infer histological information from the digital slide images;
   generating digital pathology images to display the prostate cancer-related histological information inferred from the artificial neural network model on each digital slide image; and
   providing a histological mapping image in which a tumor region extracted from each digital pathology image is mapped to a gross image of the corresponding section.

2. The method of claim 1, wherein the providing the histological mapping image comprises
   extracting a tumor region from each digital pathology image, and generating histological mapping information for mapping the extracted tumor region to the gross image of the corresponding section; and providing the histological mapping image by applying the histological mapping information to the corresponding gross image.

3. The method of claim 1, further comprising calculating a tissue area and a tumor area from each digital pathology image, and calculating a tumor burden, which is a ratio of a total tumor area to a total tissue area of a whole digital pathology image.

4. The method of claim 3, wherein the calculating the tumor burden comprises calculating the tumor area and the tumor area in units of pixels in each digital pathology image.

5. The method of claim 3, further comprising providing pathology analysis information for the prostatectomy specimen, wherein the pathology analysis information includes the tumor burden, a tumor location, and the longest diameter of the tumor.

6. The method of claim 1, wherein the providing the histological mapping image comprises providing the histological mapping image through a digital pathology image viewer installed in a user terminal.

7. The method of claim 6, further comprising providing a digital pathology image and a histological mapping image generated from the same section on one screen through the digital pathology image viewer.

8. The method of claim 1, further comprising standardizing the received digital slide image by a specified method and then inputting the standardized digital slide image into the artificial neural network model.

9. The method of claim 1, wherein the prostate cancer-related histological information inferred from the artificial neural network model includes a tumor region, and
the tumor region is displayed as a contour and/or a heatmap in the corresponding digital slide image.

10. The method of claim 1, wherein the artificial neural network model is trained using digital slide images produced from prostatectomy specimens of various institutions.

11. An apparatus for prostate cancer analysis operated by at least one processor, comprising:
an artificial neural network model that infers histological information from digital slide images produced from serial sections of a prostatectomy specimen, and
a digital pathology image viewer that displays digital pathology images including prostate cancer-related histological information inferred from the artificial neural network model, and a histological mapping image in which a tumor region extracted from each digital pathology image is mapped to a corresponding gross image.

12. The apparatus of claim 11, wherein the digital pathology image viewer displays an interface screen capable of checking, modifying, or confirming histological information inferred from the artificial intelligence model.

13. The apparatus of claim 11, wherein the digital pathology image viewer displays a tumor burden of the prostatectomy specimen, and
the tumor burden is calculated based on a tissue area and a tumor area calculated from the digital pathology images.

* * * * *